US 6,586,076 B1

(12) United States Patent
Mizutani et al.

(10) Patent No.: US 6,586,076 B1
(45) Date of Patent: **\*Jul. 1, 2003**

(54) ABSORBENT ARTICLE AND PROCESS FOR MANUFACTURING THE SAME

(75) Inventors: Satoshi Mizutani, Kagawa (JP); Etsuko Tagami, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 174 days.

This patent is subject to a terminal disclaimer.

(21) Appl. No.: 09/675,876

(22) Filed: Sep. 29, 2000

(30) Foreign Application Priority Data

Oct. 4, 1999  (JP) ............................................. 11-282489

(51) Int. Cl.[7] .............................. B32B 3/00; B32B 3/28; B32B 5/14; A61F 13/15; A61F 13/511

(52) U.S. Cl. ........................ 428/173; 428/156; 428/167; 428/170; 428/171; 428/172; 428/182; 428/183; 604/385.01; 604/378; 604/385.101

(58) Field of Search ................................ 428/156, 182, 428/167, 170–173, 183–186; 604/385.101, 385.01, 378

(56) References Cited

U.S. PATENT DOCUMENTS

| 4,546,027 A | * | 10/1985 | Holvoet et al. ............. 428/109 |
| 5,268,213 A |   | 12/1993 | Murakami et al. .......... 428/163 |
| 5,399,411 A |   | 3/1995  | Suzuki et al. ............... 428/105 |
| 5,736,219 A | * | 4/1998  | Suehr et al. ................ 428/113 |
| 5,906,879 A | * | 5/1999  | Huntoon et al. ............ 428/136 |
| 5,932,316 A | * | 8/1999  | Cree et al. .................. 428/182 |
| 5,976,665 A | * | 11/1999 | Hansson ..................... 428/136 |
| 6,010,766 A | * | 1/2000  | Braun et al. ................ 428/182 |
| 6,048,600 A | * | 4/2000  | Hansson ..................... 428/136 |
| 6,171,682 B1 | * | 1/2001 | Raidel et al. ............... 428/182 |
| 6,436,082 B1 | * | 8/2002 | Mizutani et al. ....... 604/385.01 |

FOREIGN PATENT DOCUMENTS

| DE | 4422956 A1 | 1/1996 |
| JP | 10-502000 | 2/1998 |
| WO | 96/00545 | 11/1996 |

OTHER PUBLICATIONS

PCT–WO 97/02133.*

* cited by examiner

Primary Examiner—Cheryl A. Juska
Assistant Examiner—Lynda Salvatore
(74) Attorney, Agent, or Firm—Darby & Darby

(57) ABSTRACT

There is disclosed an absorbent article including an absorbent layer and a liquid-permeable surface sheet placed on a liquid-receiving side of the absorbent layer for introducing excreted liquid from the human body to the absorbent layer. The surface sheet is of a corrugated configuration to have valleys and peaks extending in a longitudinal direction of the article and alternately arranged in a transverse direction perpendicular to the longitudinal direction. Each valley has a connecting part raised to connect between two adjacent peaks.

6 Claims, 7 Drawing Sheets

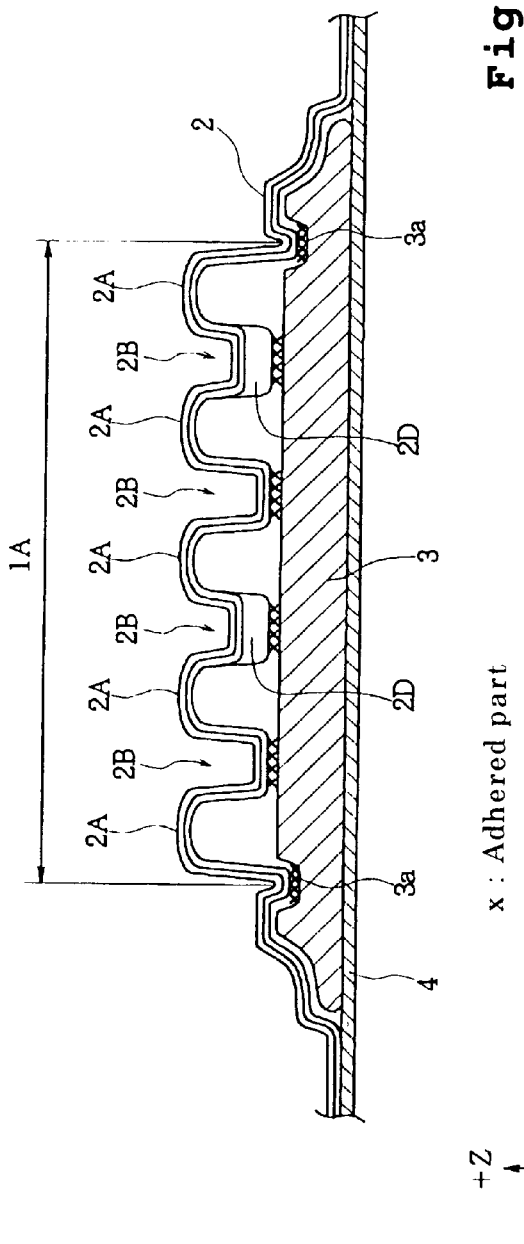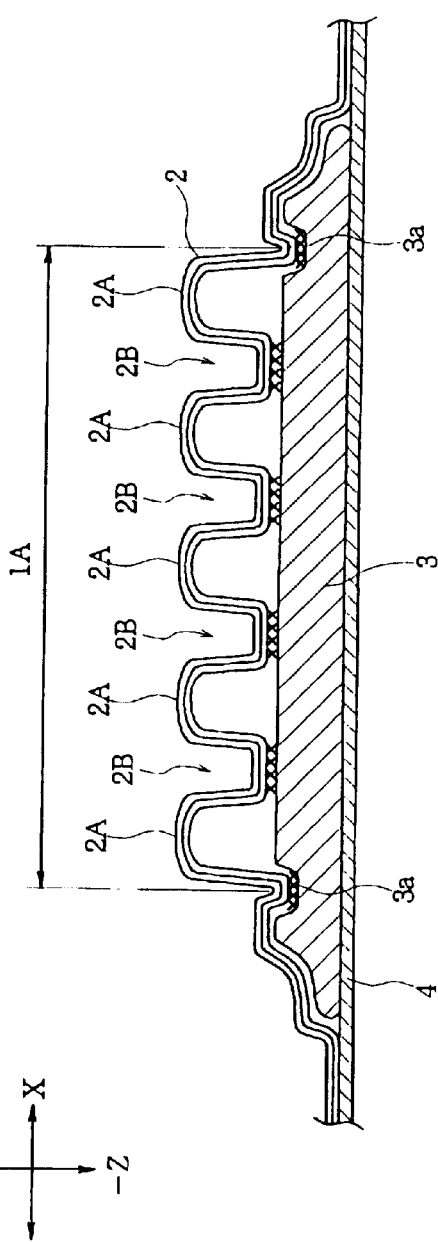

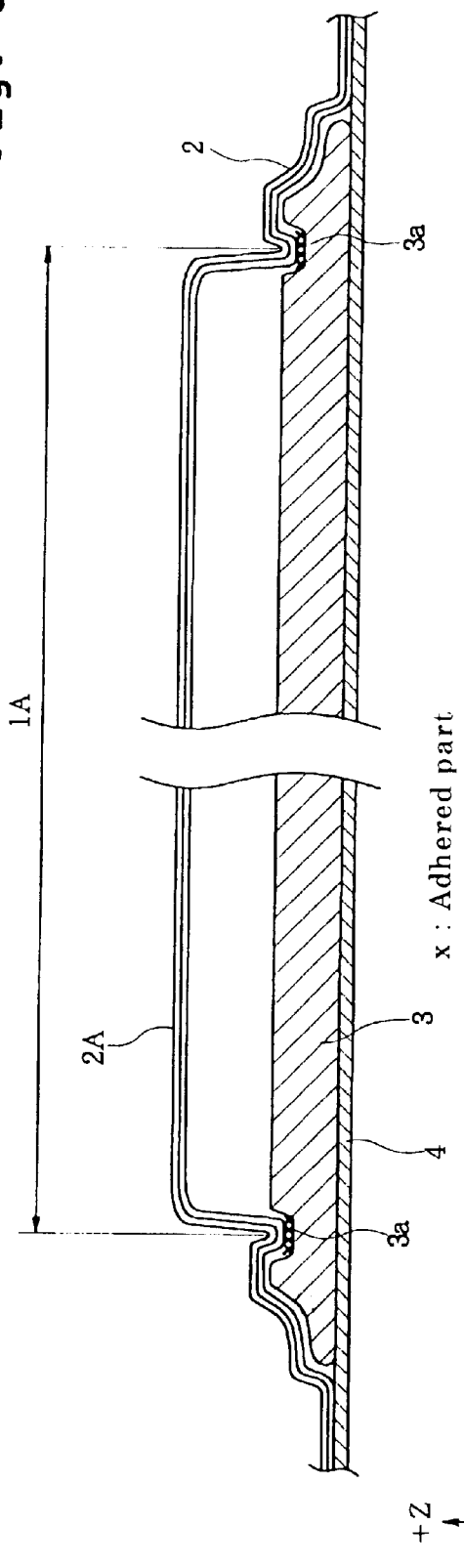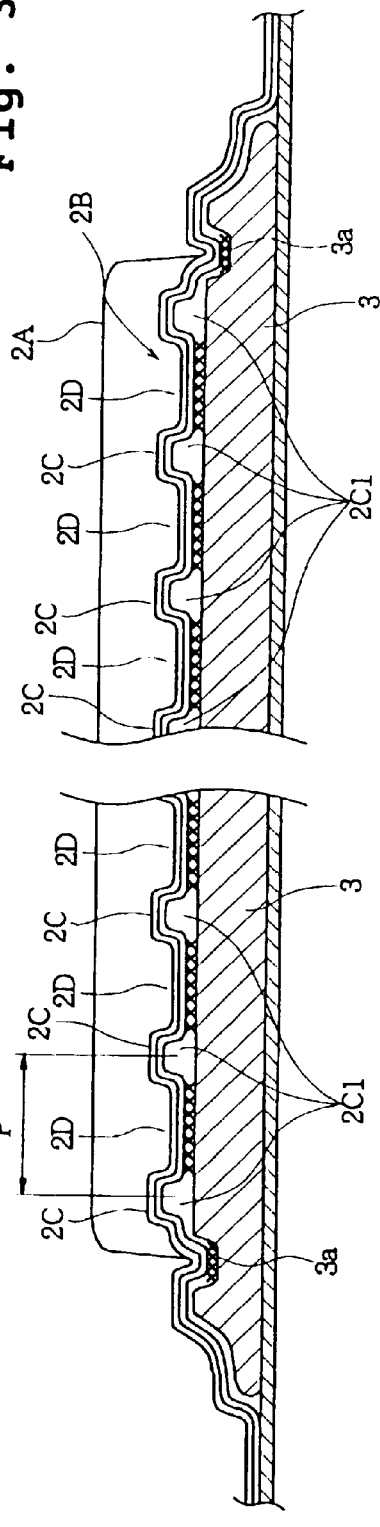

ABSORBENT ARTICLE AND PROCESS FOR MANUFACTURING THE SAME

BACKGROUND OF THE INVENTION

1. Field of the Invention

The present invention relates to an absorbent article such as sanitary napkin, panty liner and pad for incontinence and, more particularly, it relates to an absorbent article equipped with a surface sheet having good soft feeling, cushioning property and shape retaining property, and to a process for manufacturing the same.

2. Description of the Related Art

Absorbent articles having a liquid-permeable surface sheet at the liquid-receiving side of an absorbent layer are disclosed, for example, in International Unexamined Patent Publication (Kohyou) No. Heisei 10-502000.

Specifically, International Unexamined Patent Publication (Kohyou) No. Heisei 10-502000 discloses a sanitary napkin, in which a cover layer of a corrugated configuration (or wavy shape) is provided on a support layer so that the leakage of the body fluid can be prevented by the wavy shape and the flexibility of the wavy shape can make it comfortable to wear.

However, in the sanitary napkin mentioned above, the wavy shape is apt to be deformed and flattened or fall down sideways by the pressure of the user's body when the cover layer having the wavy shape touches the skin. In addition, even when the body pressure applied to the wavy shape fluctuates and is lowered upon use, the cover layer hardly restores to the original wavy shape from the flat or fallen state. As a result, the cover layer does not at all times closely touch the skin of the user in an optimum state, and there are problems that the excreted liquid spreads more than necessary on the absorbent article resulting in sideways leakage and that soft feeling to the skin and cushioning property are lowered.

SUMMARY OF THE INVENTION

The present invention has an object to provide an absorbent article which can closely contact with the user's skin at all times and which can retain soft feeling and cushioning property, and also to provide a process for manufacturing the same.

According to the invention, there is provided an absorbent article comprising an absorbent layer and a liquid-permeable surface sheet placed on a liquid-receiving side of the absorbent layer for introducing excreted liquid from the human body to the absorbent layer, wherein the surface sheet is of a corrugated configuration to have valleys and peaks extending in a longitudinal direction of the article and alternately arranged in a transverse direction perpendicular to the longitudinal direction, and wherein each valley has a connecting part raised to connect between two adjacent peaks.

In the absorbent article of the present invention, there is provided the connecting part to connect between the peaks of the surface sheet, so that the peaks are prevented from being flattened or falling down sideways readily by the pressure of user's body. Even if they are flattened or fall down sideways, in addition, the connecting part can act elastically on the peaks, when the body pressure is lowered, so that the peaks can readily restore to the original shape. That is, even when the body pressure fluctuates due to the movement of the user, the peaks can respond to the movement of the user's body to be flattened or restore to the original shape, whereby the close contact to the user's skin can be always maintained in a high level. Accordingly, the excreted liquid hardly spreads on the surface sheet to thereby prevent sideways leakage effectively. In addition, soft and cushiony feeling to the user is not lowered.

For example, the connecting part may connect side slopes of the two peaks. With the connecting part being formed to connect the side slopes of the peaks, the connected side slopes can be readily raised up, when the body pressure having been applied to the peaks is lowered, so that the peaks can readily restore to the original shape.

Preferably, each valley has a plurality of connecting parts arranged at regular intervals in the longitudinal direction. In this case, it is preferred that the interval of the connecting parts in the longitudinal direction is from 5 mm to 30 mm.

With the connecting parts in each valley being arranged at regular intervals in the longitudinal direction, as describer above, restoring ability of the corrugated configuration is improved all over the surface sheet.

Preferably, the connecting parts are staggered in the longitudinal direction, between two adjacent valleys.

With the connecting parts being arranged in such a staggered manner, the connecting parts can easily restore the individual peaks. In addition, the spread of the excreted liquid in the transverse direction is easily prevented.

Preferably, the length in the transverse direction of the top of the connecting part is from 1 mm to 10 mm.

Preferably, the height size (h) from the bottom of the valley to the top of the connecting part falls within a range of 20% to 80% the height size (H) from the bottom of the valley to the top of the peak. Below the lower limit of the aforementioned range, a restoring function of the corrugated configuration by the connecting part is lowered. Above the upper limit of the aforementioned range, on the other hand, the connecting part is apt to touch the skin whereby the feeling upon wear becomes bad.

Preferably, the surface sheet has a lower fiber density in the connecting part than in the valley exclusive of the connecting part. With the connecting part being made in such a low density as above, the excreted liquid, which tends to flow along the valleys and spread, is stopped by the connecting part.

Preferably, the surface sheet has a higher fiber density in the bottom of the valley than in the top of the peak. Also preferably, the surface sheet has a higher fiber density in the top of the peak than in the side of the peak. Also preferably, the surface sheet has a higher fiber density in the top of the peak than in the connecting part and in the side of the peak, and the fiber density in the connecting part is equal to or higher than that in the side of the peak. Most preferably, the relation of the fiber densities in respective parts of the surface sheet is (bottom of valley)>(top of peak)>(connecting part)≧(side of peak).

As a result of the above, the feeling to the skin and the cushioning property of the surface sheet can be improved. Moreover, the excreted liquid is difficult to spread in the longitudinal and widthwise directions of the valleys, so that leakage from the edges of the article in the longitudinal and transverse directions thereof can be suppressed. Accordingly, the excreted liquid is quickly absorbed by the absorbent layer through the surface sheet whereby little residual liquid remains on the surface sheet and a fresh and dry feeling can be achieved at all times.

Preferably, the back of the surface sheet is fixed to the absorbent layer at the bottom of the valley. In this case, displacement between the surface sheet and the absorbent layer hardly occurs.

Preferably, the surface sheet is a laminate of a plurality of nonwoven fabrics containing hydrophobic fibers. If it is formed by laminating a plurality of bulky nonwoven fabrics, e.g., air-through nonwoven fabrics, the surface sheet will have improved soft feeling and cushioning property.

According to the invention, there is also provided a process for manufacturing an absorbent article, comprising the steps of:
  (a) pressing a nonwoven fabric, which is supplied in a predetermined direction, between a first shaping means and a second shaping means to form a surface sheet, and
  (b) placing and fixing the surface sheet on a liquid-receiving side of an absorbent layer, wherein
    the first shaping means has ribs and grooves extending in the supplying direction of nonwoven fabric and alternately arranged in a transverse direction perpendicular to the supplying direction; the
    second shaping means has ribs and grooves extending in the supplying direction and alternately arranged in the transverse direction, each rib of which has a plurality of recesses formed at intervals in the supplying direction; and
    the surface sheet formed in the step (a) has peaks each compressed between the rib of the first shaping means and the groove of the second shaping means, valleys each compressed between the groove of the first shaping means and the rib of the second shaping means, and connecting parts raised from the valleys to connect between two adjacent peaks at the part corresponding to the recesses of the second shaping means.

BRIEF DESCRIPTION OF THE DRAWINGS

FIG. 2A is a partial cross sectional view taken along the line IIA—IIA of FIG. 1, and FIG. 2B is a partial cross sectional view taken along the line IIB—IIB of FIG. 1;

FIG. 3A is a partial cross sectional view taken along the line IIIA—IIIA of FIG. 1, and FIG. 3B is a partial cross sectional view taken along the line IIIB—IIIB of FIG. 1;

DESCRIPTION OF THE PREFERRED EMBODIMENTS

Figure 1:
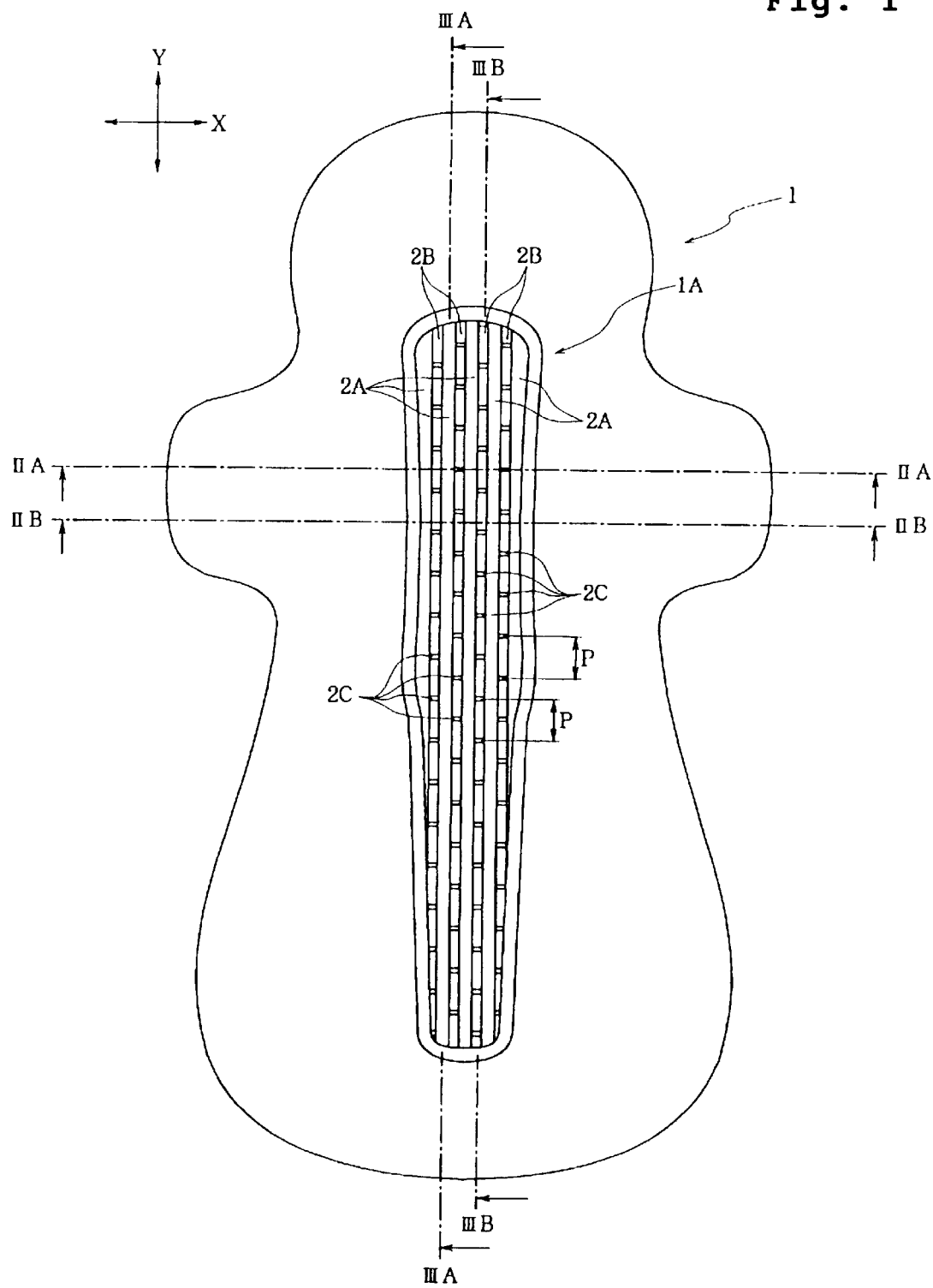
FIG. 1 is a plan view showing an absorbent article according to one embodiment of the invention, from a liquid-receiving side thereof.

As hereunder, the present invention will be illustrated by referring to the drawings.

Figure 4:
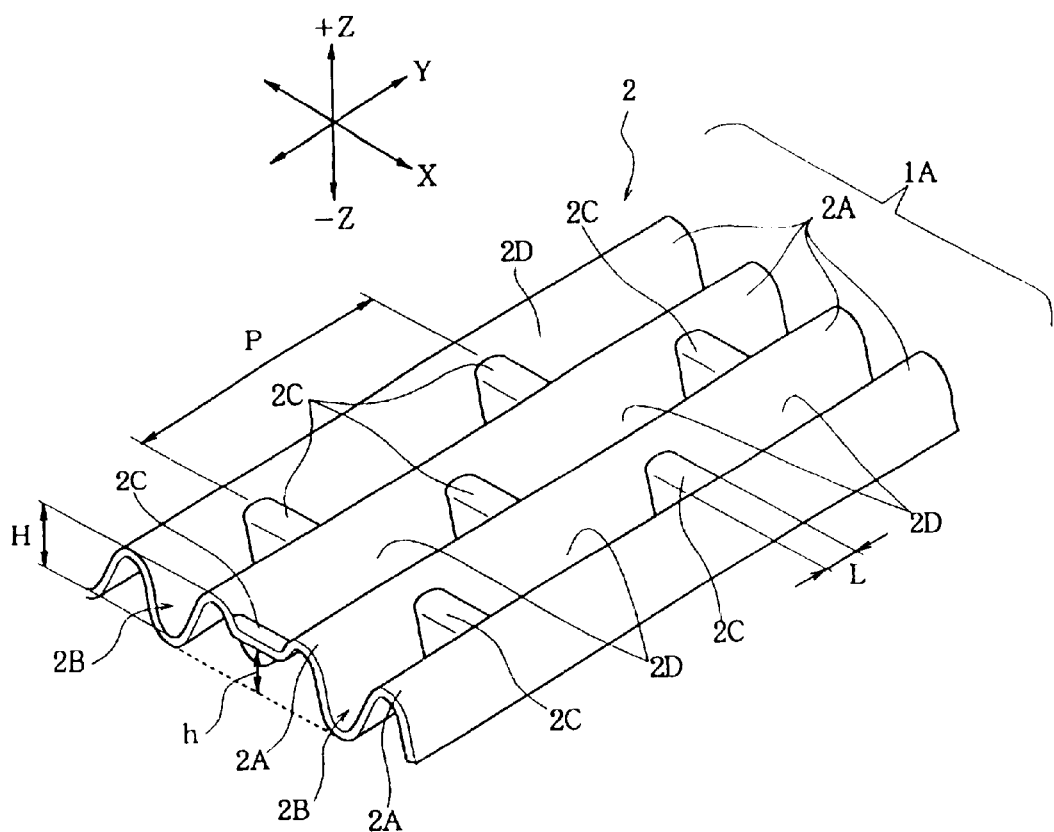
FIG. 4 is a partial perspective view of a surface sheet.

FIG. 1 is a plan view showing a sanitary napkin 1, as one embodiment of the absorbent article of the invention, from a liquid-receiving side thereof; FIGS. 2A and 2B show cross sections of FIG. 1 in the X direction, where FIG. 2A is a partial cross sectional view taken along the line IIA—IIA while FIG. 2B is a partial cross sectional view taken along the line IIB—IIB; FIGS. 3A and 3B show cross sections of FIG. 1 in the Y direction, where FIG. 3A is a partial cross sectional view taken along the line IIIA—IIIA while FIG. 3B is a partial cross sectional view taken along the line IIIB—IIIB; and FIG. 4 is a partial perspective view only of a surface sheet (the skin-contact surface) of the sanitary napkin.

As shown in FIGS. 2A and 2B, the sanitary napkin 1 is constructed to include mainly three components: a liquid-permeable surface sheet (surface structure) 2; an absorbent core (absorbent layer) 3 which absorbs excreted liquid such as menstrual blood and urine; and a liquid-impermeable back sheet 4. In use, the surface sheet 2 makes contact with the user's skin directly to receive the body fluid such as menstrual blood excreted from the human body. The body fluid thus received is passed through the surface sheet 2 and introduced into the absorbent core 3 located therebelow.

The surface sheet 2 is composed of, for example, bulky and highly-porous air-through nonwoven fabric, point-bond nonwoven fabric, spun-bond nonwoven fabric, spun-lace nonwoven fabric or melt-blown nonwoven fabric. In view of the characteristics, an air-through nonwoven fabric which is bulky and has an excellent cushioning property is most preferred.

For constituent fibers to form the above nonwoven fabrics, use can be made mainly of hydrophobic synthetic fibers. The synthetic fibers can be exemplified by those of PE (polyethylene), PP (polypropylene), PET (polyethylene terephthalate), etc.; core-sheath or side-by-side type fibers of PE/PP, PE/PET, etc.; and so on. The nonwoven fabrics may contain hydrophilic fibers such as regenerated cellulose fiber (e.g., rayon fibers) in addition to the synthetic fibers.

The fibers per se may be finished to be soft by increasing the elongation percentage by means of lowering the draft ratio upon spinning the fibers. In this case, the fibers are preferably finished to have an elongation percentage (maximum tensile strain) in a dry state of 120% or less, so that a web strength during carding of the fibers can be maintained. If the elongation percentage exceeds 120%, the web strength becomes insufficient and it is difficult to prepare a sheet. More preferably, the elongation percentage is within a range of 60% to 100%. Within this range, the web strength can be maintained to an appropriate degree, while the fibers being made sufficiently smooth.

The fineness of the fibers is preferably from 1 to 6 deniers. If the fineness is less than 1 denier, the liquid is apt to remain on the surface sheet as residual liquid due to a capillary action. If, on the other hand, the fineness is more than 6 deniers, the surface sheet may have a hard and coarse feeling.

In view of easy shaping of the sheet and prevention of the residual liquid, the basis weight (This may be referred to as "Metsuke") of the surface sheet 2 is preferably within a range of 20 g/m$^2$ to 120 g/m$^2$.

The surface sheet 2 may be a single nonwoven fabric to have a single layered structure. Alternatively, the surface sheet 2 may be a compounded sheet which is prepared by laminating two or more nonwoven fabrics, as shown in FIGS. 2A to 3B. It is optimum that the basis weight of the surface sheet 2 having the single layered structure is 85 g/m$^2$.

When the surface sheet 2 is a three-layered compounded sheet, for example, the uppermost one of the three layers may be a nonwoven fabric prepared by sheeting PE/PET fibers of a core-sheath type (fineness of 2.5 deniers, fiber length of 51 mm) according to an air-through method to have a basis weight of 30 gm$^2$, a CD strength of 190 g/inch and a thickness of about 0.5 mm. In this case, the core-sheath type fibers of the uppermost (first) layer to contact the user's skin in use is preferably of a filled-up (or dense) structure to have less tension thereby to improve the feeling to the touch. On the other hand, the intermediate and lowermost (second and third) layers are preferably formed of core-sheath type fibers of a hollow structure to be highly bulky and to have an improved soft feeling. Moreover, the skin-contact side (front surface) of the first layer is preferably added with more titanium oxide to reduce the so-called elasticity of the fibers thereby to improve the feeling to the tough. More specifically, in the second layer, the third layer, and the back surface (non-skin-contact side) of the first layer, the content of titanium oxide in the core component of the core-sheath structure is 0.5%. On the other hand, in the skin-contact side of the first layer, the content of titanium oxide is 4%.

As shown in FIG. 1, at the center of the surface sheet 2 of the sanitary napkin 1, there is formed a skin-contact part 1A of a nearly violin-shape. As shown in FIGS. 2A and 2B, along the periphery of the absorbent core 3 placed on the back sheet 4, the absorbent core 3 and surface sheet 2 are pressed together to form a pressed part 3a. At this pressed part 3a, moreover, the absorbent core 3 and surface sheet 2 are fixed to each other by means of adhesion using a hot melt adhesive, thermal fusion, or the like. The skin-contact part 1A is confined within the pressed part 3a.

As shown in FIGS. 1, 2A, 2B, 3A, 3B and 4, the skin-contact part 1A is of a corrugated configuration (or wavy shape) to have peaks 2A and valleys 2B extending in the longitudinal direction (Y direction) of the sanitary napkin 1 and alternately arranged in the transverse direction (X direction) of the sanitary napkin 1. As shown in FIG. 3B and FIG. 4, in each valley 2B, there is formed a connecting part 2C rising in a convex manner (i.e., rising from the bottom of the valley 2B in the +Z direction). The connecting part 2C extends in the transverse direction (X direction) to connect side slopes of two peaks 2A and 2A, which are located at the sides of the valley 2B. Each valley 2B has a plurality of connecting parts 2C.

In each valley 2B, these connecting parts 2C are arranged at regular intervals P in the longitudinal direction to thereby form a long groove 2D between two connecting parts 2C. The length in the transverse direction of the top of the connecting part 2C is preferably within a range of 1 mm to 10 mm, more preferably, within a range of 2 mm to 6 mm. If it is less than 1 mm, the connecting part 2C hardly contributes to the restoration of the corrugated configuration. If, on the other hand, it is more than 10 mm, the corrugated configuration does not provide sufficient soft feeling and therefore, it becomes so rigid as to cause hard creases disadvantageously.

The interval P (nearly the length of the long groove 2D) is preferably within a range of 5 mm to 30 mm, more preferably, within a range of 5 mm to 20 mm. If the interval P is more than 30 mm, the shape restoring property of the corrugated configuration having the peaks 2A and the valleys 2B will be lowered. If, on the other hand, the interval P is less than 5 mm, rigid feeling will increase to cause hard creases, and soft feeling by the corrugated configuration will be impaired.

As shown in FIG. 4, the height (h) from the bottom of the valley 2B to the top of the connecting part 2C preferably falls within a range of 20% to 80% the height (H) from the bottom of the valley 2B to the top of the peak 2A. Here, the heights (H) and (h) are measured in the Z direction. If the height (h) is less than the lower limit of the aforementioned range, the connecting part 2C hardly contributes to the restoration of the corrugated configuration. If, on the other hand, the height (h) is more than the upper limit of the aforementioned range, the connecting part 2C is liable to contact with the user's skin thereby to provide uncomfortable feeling to the user.

In the course of the formation of the corrugated configuration, the surface sheet 2 is pressed more forcibly in the long groove 2D (the part exclusive of the connecting part 2C, of the valley 2B) than in the connecting part 2C. Therefore, in the surface sheet 2, the long groove 2D has a higher fiber density than that of the connecting part 2C. With the fiber density of the connecting part 2C being made so lower, the connecting part 2C can be made elastic. Accordingly, when the peaks 2A are crushed, they can be readily restored to the original shape by the recovery of the connecting part 2C.

When the excreted liquid is given to the surface sheet 2, the liquid is apt to spread along the long groove 2D (i.e., between two peaks 2A and 2A), but is stopped by the connecting part 2C having a low fiber density. Thus, the excreted liquid is prevented from spreading more than necessary on the surface sheet 2. The liquid confined within the long groove 2D is passed into the absorbent core 3 through the surface sheet 2. As a result, the sanitary napkin 1 can absorb the excreted liquid reliably while preventing sideways leakage.

Further, when the fiber density of the surface sheet 2 is made in such a manner that (bottom of valley 2B)>(top of peak 2A)>(connecting part 2C)≧(side slope of peak 2A), the following effects can be expected.

Firstly, when the fiber density at the top of the peak 2A is made lower than that of the bottom of the valley 2B, feeling to the touch can be improved.

Secondly, when the fiber density of the side slopes of the peaks 2A and 2A located at the sides of the valley 2B is made lower than that of the top of the peak 2A, cushioning property can be improved and feeling to the touch can also be improved.

Thirdly, although the excreted liquid given to the bottom of the valley 2B is apt to spread quickly in the longitudinal direction of the surface sheet 2, the excreted liquid on the bottom of the valley 2B is prevented from spreading by the connecting part 2C and the side slopes, since the fiber densities of the connecting part 2C and the side slopes are relatively lower than that of the bottom of the valley 2B. This results in the suppression of spread of the liquid all over the surface sheet 2 in the longitudinal and transverse directions, whereby leakage of the excreted liquid can be prevented.

Fourthly, the rate of absorption of liquid is higher in the part having a higher fiber density than in the part having a lower fiber density. Accordingly, the excreted liquid flown into the long groove 2D can be quickly introduced into the absorbent core 3 through the bottom of the valley 2B. Therefore, the excreted liquid is difficult to spread in the longitudinal and the transverse directions of the valley whereby the leakage from the edges of the napkin in the transverse and the longitudinal directions can be suppressed. In addition, the excreted liquid can be quickly absorbed into the absorbent core 3 through the surface sheet 2, so that no residual liquid is present on the surface sheet 2 to thereby provide a fresh and dry feeling at all times.

In the sanitary napkin 1 using the surface sheet 2, the two adjacent peaks 2A are connected by the connecting part 2C formed in the valley 2B therebetween, so that the elongation of the surface sheet 2 in the transverse direction (X direction) can be suppressed. Accordingly, the deformation of the peak 2A such as crushing in flat or falling sideways due to the application of the pressure of the user's body to the skin-contact part 1A can be made difficult to occur.

Even if a large pressure is applied from the user's body to the skin-contact part 1A and the peaks 2A are crushed resulting in deformation of the corrugated configuration, on the other hand, the peaks 2A can rise up by the elasticity of the connecting part 2C when the body pressure is decreased due to the movement of the user's body. In addition, even if the surface sheet 2 becomes flat in such a manner that the peak 2A and the peak 2A expand in the transverse direction (X direction), those peaks 2A and 2A are drawn due to a tensile elasticity in the transverse direction of the connecting part 2C whereby the surface sheet 2 can be easily restored to the corrugated configuration from the flat state.

Therefore, the peaks and valleys of the surface sheet 2 follow the movement of the user's body whereby the peaks 2A of the surface sheet 2 always touches the skin of the user at an optimum pressure. Accordingly, sideways leakage of the excreted liquid can be prevented and, in addition, soft feeling and cushiony feeling can be maintained at all times.

As shown in FIG. 4, the connecting part 2C provided in the valley 2B connects the slopes of the peaks 2A at the sides thereof and does not connect the tops of the peaks 2A. Therefore, the excreted liquid excreted into one long groove 2D is hardly flown into another long groove 2D adjacent thereto in the transverse direction over the peak 2A. Due to that reason, sideways leakage of the excreted liquid in the transverse direction can be prevented as well.

Further, between two adjacent valleys 2B and 2B, the connecting parts 2C are formed in such a manner that they are displaced with respect to each other in the longitudinal direction, that is; they are staggered in the longitudinal direction. As a result, the connecting parts 2C are formed alternately in the transverse direction. With the connecting parts 2C being formed alternately in the transverse direction as above, the restoring force can be given to all the peaks 2A. In this case, moreover, since the long grooves 2D having the connecting parts 2C at the ends thereof are also formed alternately in the transverse direction, even if the excreted liquid moves to the adjacent valley 2B along the connecting part 2C, the excreted liquid is retained in the long groove 2D and hardly moves to the further next valley 2B. This also prevents the sideways leakage effectively.

As shown in FIGS. 2A, 2B and 3B, the back of the surface sheet 2 is partially fixed to the absorbent core 3 at the long grooves 2D (the valleys 2B exclusive of connecting parts 2C) by means of an adhesive or the like. This prevents the displacement between the absorbent core 3 and the surface sheet 2.

Furthermore, in the state where the skin-contact part 1A is actually brought into contact with the user's skin, the entire sanitary napkin 1 is bent in the longitudinal direction (Y direction) to fit the user's body. In this, the connecting parts 2C are arranged at intervals in the longitudinal direction and, in addition, the fiber density of the connecting parts 2C is lower than that of the other parts. Accordingly, the surface sheet 2 is apt to be bent where the connecting part 2C serves as a bending point. Due to the bending, the corrugated configuration is hardly crushed. Therefore, a close contact of the surface sheet 2 to the user is improved.

Hereinafter, a process for manufacturing the sanitary napkin (absorbent article) will be illustrated.

Figure 5:
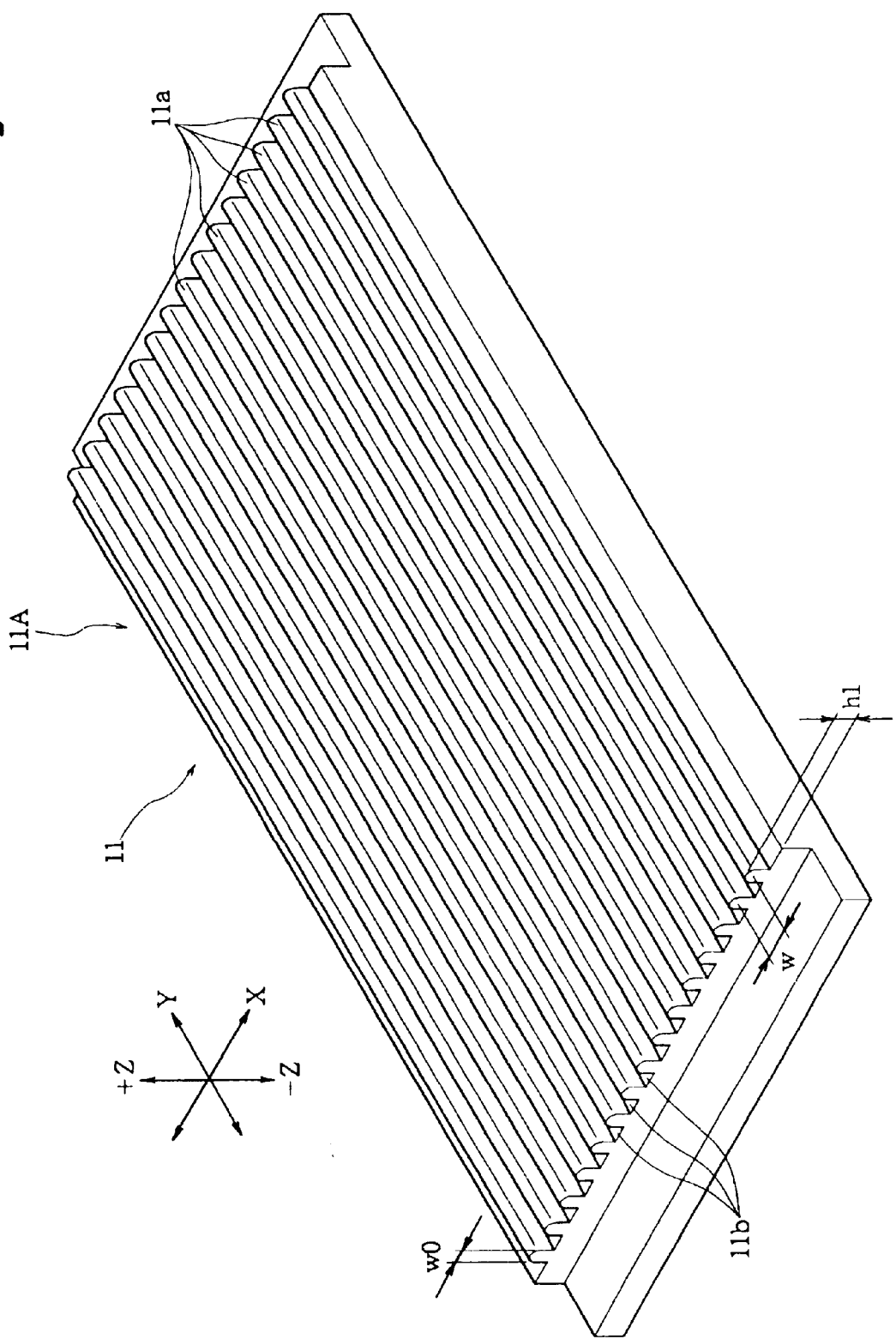
FIG. 5 is a perspective view of a multi-row mold for shaping the surface sheet to have a corrugated configuration.
Figure 6:
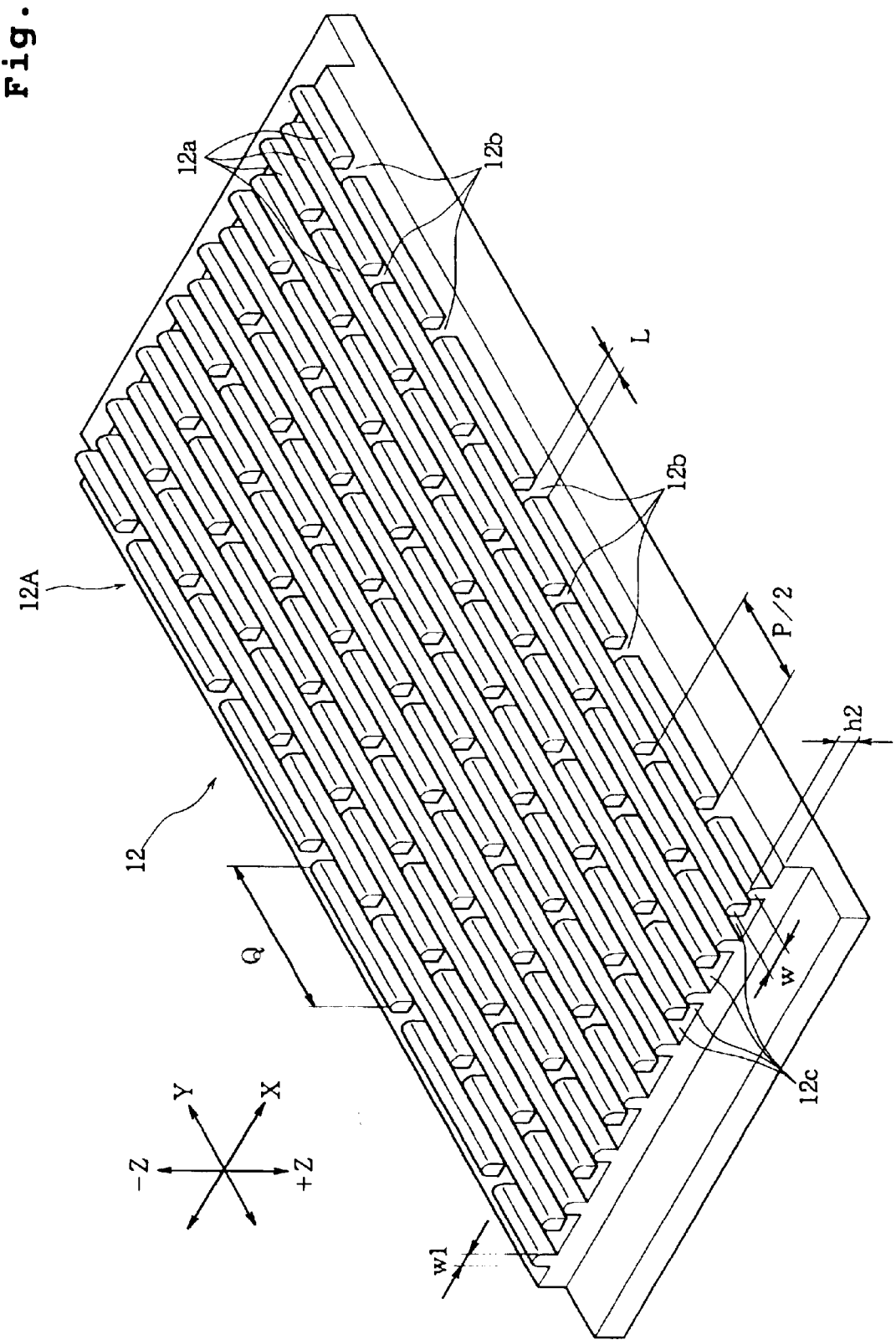
FIG. 6 is a perspective view of a convex mold for shaping the surface sheet to have a corrugated configuration.

FIG. 5 and FIG. 6 show molds (shaping means) for forming the corrugated configuration of the surface sheet.

FIG. 5 is a perspective view of a multi-row mold 11 (as a first shaping means) and FIG. 6 is a perspective view of a convex mold 12 (as a second shaping means).

In the multi-row mold 11 (the first shaping means) shown in FIG. 5, the +Z side shown in the drawing is a pushing surface 11A. In the pushing surface 11A, a plurality of convex ribs 11a, which continuously extend in the longitudinal direction (Y direction) and project in a convex shape in their cross section, are arranged at regular intervals W. Between two convex ribs 11a and 11a, there is formed a groove 11b. Here, when the width of the convex rib 11a is w0, its relation with the interval W (for the transverse arrangement of the convex ribs 11a) is W>w0.

In the convex mold 12 (the second shaping means) shown in FIG. 6, the −Z side shown in the drawing is a pushing surface 12A. In the pushing surface 12A, a plurality of convex ribs 12a having a predetermined length Q are arranged in the longitudinal direction. Between two convex ribs 12a and 12a adjacent to each other in the longitudinal direction (Y direction), there is formed a recess (or hollow) 12b having a predetermined length L. Between two convex ribs 12a and 12a adjacent to each other in the transverse direction (X direction), there is formed a groove 12c. The length Q of the convex rib 12a plus the length L of the recess 12b is equal to the interval P of the aforementioned connecting parts 2C.

In the convex mold 12 shown in FIG. 6, moreover, recesses 12b formed in any one of rows in which the convex ribs 12a are arranged in the longitudinal direction (i.e., recesses 12b formed in a first row) are displaced by the length of P/2, which is nearly one-half of the length Q of the convex rib 12a, with respect to recesses 12b formed in a second row adjacent to the first row. That is, a recess 12b in the (n+1)-th row and a recess 12b in the (n−1)-th row are located at the midpoint between a recess 12b in the (n)-th row and another recess 12b adjacent thereto in the longitudinal direction in the same (n)-th row.

These rows of the convex ribs 12a are arranged at regular intervals W in the transverse direction. As in the multi-row mold 11, when the width of the convex rib 12a is w1, its relation with the interval W of the convex ribs 12a in the transverse direction is W>w1.

Here, between the width w0 of the convex rib 11a of the multi-row mold 11 and the width w1 of the convex rib 12a of the convex mold 12, there is a relation of w0>w1.

The multi-row mold 11 and convex mold 12 form a set of embossing die assembly. A nonwoven fabric to form the surface sheet 2 is placed on the multi-row mold 11 with the pushing surface 11A being directed upward. Then, the nonwoven fabric is pressed from the above by the convex mold 12 with the pushing surface 12A being directed downward. As a result, there is formed the corrugated configuration shown in FIG. 4.

Here, the nonwoven fabric is pressed between the convex rib 11a of the multi-row mold 11 (the first shaping means) and the groove 12c of the convex mold 12 (the second shaping means) whereupon the peak 2A is formed. In addition, the nonwoven fabric is pressed between the convex rib 12a of the convex mold 12 and the groove 11b of the multi-row mold 11 whereupon the valley 2B is formed. Further, at the part corresponding to the recess 12b of the convex mold 12, the nonwoven fabric is formed with the connecting part 2C which is located within the valley 2B and raised into a convex shape. Since the pressure applied to the connecting part 2C between the molds 11 and 12 is relatively low, the fiber density of the connecting part 2C becomes low, as has been already described, as compared with the peak 2A and valley 2B.

Moreover, there is a relation of w0>w1 where w0 is the width of the convex rib 11a of the multi-row mold 11 while w1 is the width of the convex rib 12a of the convex mold 12. Accordingly, the size in the transverse direction of the valley 2B becomes smaller than the size in the transverse direction of the peak 2A, as shown in FIG. 2A.

Figure 7:
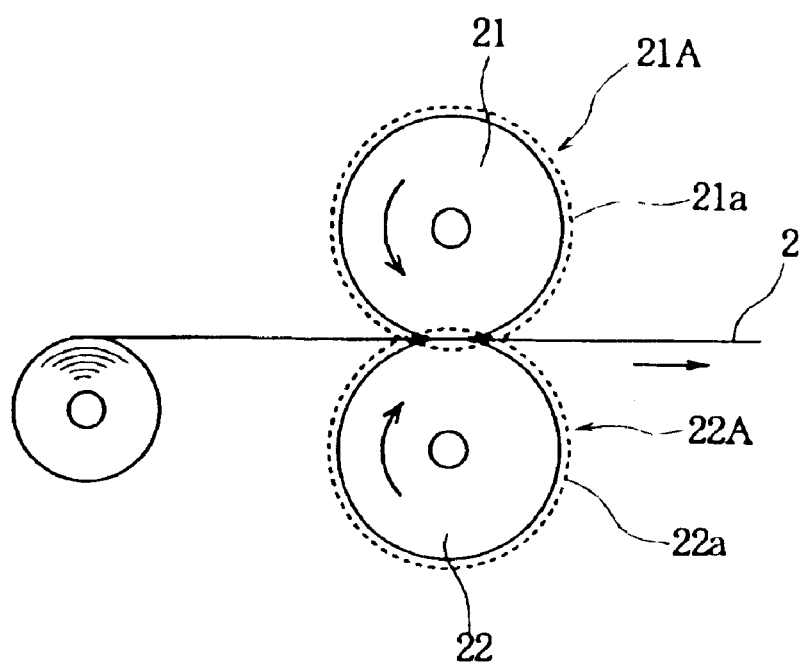
FIG. 7 is a schematic view of another method for shaping a surface sheet.

FIG. 7 is a schematic diagram showing another step for forming the corrugated configuration of the surface sheet.

In FIG. 7, the outer peripheral surfaces of two rollers are opposed to each other. The numeral 21 indicates a roller where the surface shape of the multi-row mold 11 (the first shaping means) is arranged as a roll; the numeral 22 indicates a roller where the surface shape of the convex mold 12 (the second shaping means) is arranged as a roll.

The roller 21 rotates counterclockwise while the roller 22 rotates clockwise. The relationship between the roller 21 and the roller 22 is such that a convex rib 22a of the roller 22 comes between convex ribs 21a and 21a of the roller 21. Accordingly, when a band-shaped nonwoven fabric (such as a multi-layered nonwoven fabric) is inserted between the roller 21 and the roller 22 from the left end of the drawing, the corrugated configuration of the peaks 2A and valleys 2B, in which the connecting parts 2C are formed at regular intervals P in the valleys 2B, are continuously formed on the nonwoven fabric and let out from the right end of the roller 21 and the roller 22. This nonwoven fabric is used for the surface sheet 2.

It is preferred that the molds 11 and 12 or the rollers 21 and 22 are both heated at 70° C. to 160° C. This improves the moldability of the corrugated configuration and the connecting part 2C, as compared with the case where the nonwoven fabric is merely pressed between molds without heating, and therefore, they are prevented from getting out of shape. Alternatively, before the pressing step with the molds 11 and 12 or the rollers 21 and 22, the nonwoven fabric may be preheated by passing through preheating rollers heated at 70° C. to 160° C., or by blowing a hot air, for example.

Further, after the shaping step by pressing under heat, for example, a cold air may be blown to the nonwoven fabric. This can make the distortion of the shape much less during conveyance.

In the manufacturing process of the sanitary napkin 1, the absorbent core 3 is placed on the back sheet 4, and the surface sheet 2 thus prepared is superposed above the absorbent core 3 and the peripheral portions of the back sheet 4 outside, the absorbent core 3. Here, a hot melt adhesive is partially applied to the absorbent core 3, at the surface on the liquid-receiving side thereof. The hot melt adhesive is also applied to the back sheet 4. As a result of adhesion by means of the hot melt adhesive, a laminate of the back sheet 4, the absorbent core 3 and the surface sheet 2 is formed to have such a cross-sectional structure as shown in FIGS. 2A and 2B.

The above-mentioned laminate is further sandwiched and pressed between pressure rollers under heat to thereby form the pressed part 3a in such a violin shape as shown in FIG. 1.

EXAMPLE

A sanitary napkin including a corrugated surface sheet (A) formed with connecting parts 2C and another sanitary napkin including a corrugated surface sheet (B) with no connecting part were prepared and subjected to evaluation tests. Details are described hereinbelow.

(Specification of a Compounded Sheet to be Used for Surface Sheets)

PE (polyethylene)/PET (polyethylene terephthalate) core-sheath type fibers having a fineness of 2.5 deniers and a fiber length of 51 mm were made into a sheet form by air-through method to prepare a nonwoven fabric having a basis weight of 30 g/m$^2$, a CD strength of 190 g/inch and a thickness of 0.5 mm. Three sheets thereof were laminated to form a compounded sheet.

(Specification of the Corrugated Surface Sheet (A) Formed With Connecting Parts)

The multi-row mold 11 (See FIG. 5) where the height h1 of the convex rib 11a was 5 mm and the interval W in the transverse direction was 5 mm and the convex mold 12 (See FIG. 6) where the height h2 of the convex rib 12a was 3.5 mm, the length L of the recess 12b was 2 mm and the length Q of the convex rib 12a was 2.5 mm were heated at 80° C. and 90° C., respectively, and the aforementioned compounded sheet was pressed and heated for 1 second under a compression of 50 kgf whereupon a corrugated surface sheet formed with connecting parts 2C was prepared.

(Specification of the Corrugated Surface Sheet (B) with No Connecting Part)

Two multi-row molds 11 identical to above (height h1=5 mm; interval W in the transverse direction=5 mm) were prepared and the aforementioned compounded sheet was pressed between the two multi-row molds from top and bottom whereupon a corrugated surface sheet with no connecting part was prepared.

(1) Test for Evaluating Shape-restoring Property.
(Specification of Samples)

Each of the aforementioned surface sheets (A) and (B) was cut into a size of 50 mm×50 mm and placed on an absorbent core 3 which was prepared by blending wood pulp having a basis weight of 120 g/m$^2$ with SAP (Super Absorbent Polymer) of 30 g/m$^2$ followed by pressing into a flat shape to have a thickness of 2 mm, to thereby prepare a sample of a sanitary napkin.

(Test Method for Evaluating Shape-restoring Property)

7 ml of liquid (artificial menstrual blood) was dropped onto the surface sheet of each sample at the flow rate of 7 ml/minute and allowed to stand for 30 seconds.

After standing, each sample piece was applied with a load of 50 g/cm$^2$ for 5 minutes and the height H1 of the peak 2A after the load was released was measured. Also, the height H0 of the peak 2A before applying the load was measured.

It was defined that (shape-restoring rate)=[(height H1 after applying load)/(height H0 before applying load)]×100 and an evaluation was carried out by comparing the surface sheet (A) with the surface sheet (B).

(Result of the Test for Evaluating Shape-restoring Property)

A: shape-restoring rate of the corrugated surface sheet formed with connecting parts=60%

B: shape-restoring rate of the corrugated surface sheet with no connecting part=40%

(2) Test for Evaluating Restoration from Compression
(Specification of Samples)

The sample was nearly the same as that for the above-mentioned test for evaluating the shape-restoring property except that the size of the individual surface sheets (A) and (B) was made 50 mm×100 mm.

(Test Method for Evaluating Restoration from Compression)

7 ml of artificial menstrual blood was absorbed by each sample.

A load of 3 g/m$^2$ was applied to each sample and the thickness (a) under the load was measured.

Then each sample was applied with a load of 47 g/m² and allowed to stand for 10 minutes.

After standing, the load was returned to 3 g/m² and allowed to stand for 3 minutes and the thickness (b) of each sample was measured.

Restoring rate (%) from compression of each sample was calculated from the formula that restoring rate (%)=(b/a)×100.

(Result of the Test for Evaluating Restoration from Compression)

A: the restoring rate from compression of the corrugated surface sheet formed with connecting parts=55% or more B: the restoring rate from compression of the corrugated surface sheet with no connecting part=50% or less As understood from the results of the evaluation tests, the corrugated surface sheet (A) formed with the connecting parts is better than the corrugated surface sheet (B) with no connecting part in both terms of shape-restoring rate and restoring rate from compression.

In the corrugated surface sheet formed with the connecting parts, moreover, it is possible to adjust the, shape-restoring rate and the restoring rate from compression by increasing or decreasing the connecting parts in number.

As has been described in detail hereinbefore, the absorbent article of the invention has excellent soft feeling and cushioning property.

In addition, when the body pressure applied to the surface sheet is released, the soft feeling and cushioning property can be restored to the initial state prior to application of the body pressure.

Here, 'comprises/comprising' when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. An absorbent article comprising an absorbent layer and a liquid-permeable surface sheet placed on a liquid-receiving side of the absorbent layer for introducing excreted liquid from the human body to the absorbent layer, wherein the surface sheet comprises a corrugated nonwoven fabric having peaks and valleys extending in a longitudinal direction of the article and alternating with each other in a transverse direction perpendicular to the longitudinal direction, wherein in each valley, the nonwoven fabric is further raised at regular intervals in the longitudinal direction to form connecting portions, each connecting portion extending between transversely opposed side slopes of the corrugated nonwoven fabric.

2. The absorbent article as set forth in claim 1, wherein the back of the surface sheet is fixed to the absorbent layer at the bottom of the valley.

3. The absorbent article as set forth in claim 1, wherein the surface sheet is a laminate of a plurality of nonwoven fabrics containing hydrophobic fibers.

4. The absorbent article as set forth in claim 1, wherein connecting portions in one valley are offset from connecting portions in an adjacent valley in the longitudinal direction.

5. The absorbent article as set forth in claim 4, wherein an interval of the connecting portions in the longitudinal direction is from 5 mm to 30 mm, a length of a top of each connecting portion in the transverse direction is from 1 mm to 10 mm, and a height (h) from a bottom of the valley to the top of the connecting portion falls within a range of 20% to 80% of a height (H) from the bottom of the valley to a top of the peak.

6. The absorbent article as set forth in claim 5, wherein the surface sheet has a fiber density in accordance with the following relationship:

valley-bottom density>peak-top density>connecting portion density≧side slope density.

* * * * *